United States Patent
Suzuki et al.

(10) Patent No.: US 8,882,731 B2
(45) Date of Patent: Nov. 11, 2014

(54) DEFECATION DETECTION APPARATUS

(75) Inventors: Miou Suzuki, Kagawa (JP); Yoshihisa Fujioka, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 137 days.

(21) Appl. No.: 13/503,499

(22) PCT Filed: Oct. 15, 2010

(86) PCT No.: PCT/JP2010/068123
§ 371 (c)(1), (2), (4) Date: Jun. 13, 2012

(87) PCT Pub. No.: WO2011/049010
PCT Pub. Date: Apr. 28, 2011

(65) Prior Publication Data
US 2012/0245541 A1    Sep. 27, 2012

(30) Foreign Application Priority Data

Oct. 23, 2009    (JP) ................. 2009-244824

(51) Int. Cl.
| | |
|---|---|
| *A61M 1/00* | (2006.01) |
| *A61F 13/42* | (2006.01) |
| *A61F 13/84* | (2006.01) |
| *G01N 25/18* | (2006.01) |
| *A61F 5/441* | (2006.01) |
| *A61F 5/451* | (2006.01) |

(52) U.S. Cl.
CPC ............. *A61F 5/451* (2013.01); *A61F 13/42* (2013.01); *A61F 5/441* (2013.01); *A61F 13/84* (2013.01); *G01N 25/18* (2013.01)
USPC .......... 604/319; 604/317; 604/318; 604/327; 604/329; 604/358; 340/603; 340/604; 340/605

(58) Field of Classification Search
CPC ............ A61M 1/00; A61F 5/44; A61F 13/20; A61F 5/48; H01H 29/00; G08B 21/00; G08B 23/00
USPC ................... 604/317, 318, 319, 327
See application file for complete search history.

(56) References Cited

U.S. PATENT DOCUMENTS 8,274,393 B2 *   9/2012   Ales et al. ............... 340/604
2011/0040267 A1 * 2/2011   Wada et al. ............. 604/318

FOREIGN PATENT DOCUMENTS

| JP | 2001-318067 A | 11/2001 |
|---|---|---|
| JP | 2002-143199 A | 5/2002 |

(Continued)

OTHER PUBLICATIONS

International Search Report from corresponding PCT application No. PCT/JP2010/068123 dated Jan. 18, 2011 (2 pgs).

(Continued)

*Primary Examiner* — Tatyana Zalukaeva
*Assistant Examiner* — Ilya Treyger
(74) *Attorney, Agent, or Firm* — Brinks Gilson & Lione

(57) ABSTRACT

A defecation detection apparatus including: a feces/urine receiving member that is placed to face the body of a wearer and that receives discharged feces and urine; a urine suction device that is detachably attached to the feces/urine receiving member and that can sucks urine discharged in the feces/urine receiving member; a temperature sensor that is placed at a defecation position where discharged feces are received in the feces/urine receiving member; and a control section that detects the presence of discharged feces based on a signal remaining after removing a signal that is output from the temperature sensor within a predetermined time after an operation of the urine suction device from a signal that is output from the temperature sensor.

14 Claims, 10 Drawing Sheets

(56) References Cited

FOREIGN PATENT DOCUMENTS

| | | |
|---|---|---|
| JP | 2002-301098 A | 10/2002 |
| JP | 2008-013501 | 2/2008 |
| JP | 2008-43501 A | 2/2008 |
| JP | 2009-1423860 A | 7/2009 |
| KR | 2008-0111917 A | 11/2007 |
| WO | WO 2009/052496 A1 | 4/2009 |
| WO | WO 2009/101738 A1 | 8/2009 |

OTHER PUBLICATIONS

Chinese Office Action and English translation from corresponding Chinese application No. 201080047630.4 dated Dec. 18, 2013 (13 pgs).

European extended Search Report from corresponding European application No. 10824859.2 dated Mar. 6, 2014 (6 pgs).

* cited by examiner

US 8,882,731 B2

DEFECATION DETECTION APPARATUS

RELATED APPLICATION

The present application is a 35 U.S.C. §371 national stage filing of International Patent Application No. PCT/JP2010/068123, filed Oct. 15, 2010, to which priority is claimed under 35 U.S.C. §120 and through which priority is claimed under 35 U.S.C. §119 to Japanese Priority Patent Application No. 2009-244824, filed Oct. 23, 2009.

TECHNICAL FIELD

The present invention relates to a defecation detection apparatus.

BACKGROUND ART

For example, there is already known a device which detects defecation and urination based on a signal that is output from a temperature sensor placed in a diaper (see Patent Document 1, for example). Such a device determines whether it is urine or feces that has been discharged based on the difference in the course of a temperature rise which is detected from the signal output from the temperature sensor placed in the diaper. Also, there is known an apparatus which is provided with a suction device for sucking urine and whose function is to suck urine when urination is detected. In such an apparatus having the urine suction function, the diaper is ventilated when the suction device is operated.

PRIOR ART DOCUMENTS

Patent Documents

[Patent Document 1] JP 2002-301098A

SUMMARY OF INVENTION

Problems to be Solved by the Invention

When urine is sucked by the suction device, the temperature in the diaper changes rapidly. In this case, there is the following problem: when detecting such a temperature change in the diaper from the signal that is output by the temperature sensor, a control section may determine erroneously whether either urine or feces has been discharged, making it impossible to correctly determine the presence of discharged feces.

The invention has been contrived in view of the problem described above, and an advantage thereof is to provide a defecation detection apparatus which can detect correctly the presence of discharged feces without being affected by the operation of the urine suction device.

Means for Solving the Problems

An aspect of the invention to achieve the above advantage is a defecation detection apparatus including:

a feces/urine receiving member that is placed to face the body of a wearer and that receives discharged feces and urine;

a urine suction device that is detachably attached to the feces/urine receiving member and that can suck urine discharged in the feces/urine receiving member;

a temperature sensor that is placed at a defecation position where discharged feces are received in the feces/urine receiving member; and a control section that detects the presence of discharged feces based on a signal remaining after removing a signal that is output from the temperature sensor within a predetermined time after an operation of the urine suction device from a signal that is output from the temperature sensor.

Other features of this invention will become apparent from the description in this specification and the attached drawings.

Effects of the Invention

According to the present invention, a defecation detection apparatus which can correctly detect the presence of discharged feces without being affected by the operation of a urine suction device is achieved.

DESCRIPTION OF EMBODIMENTS

Figure 1:
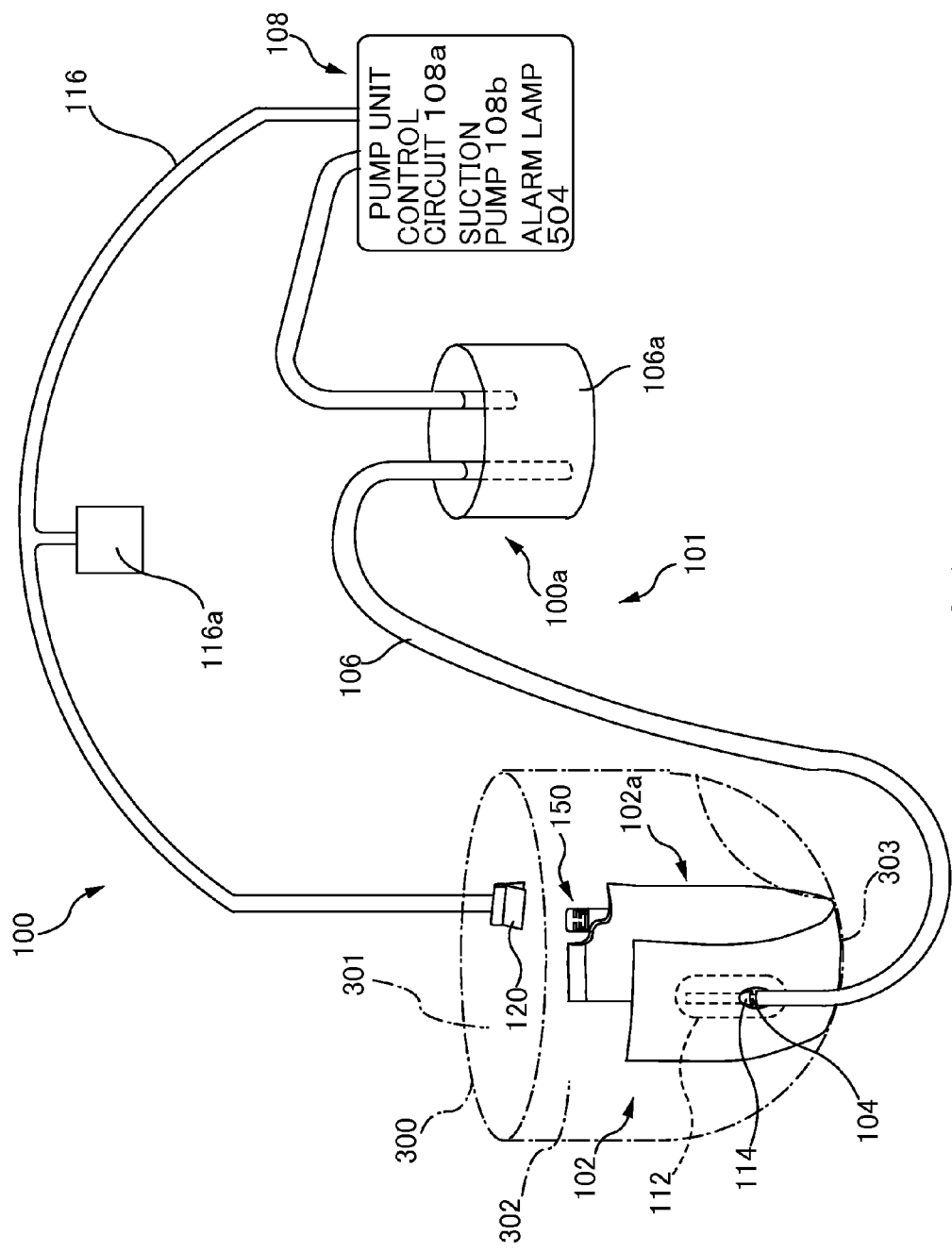
FIG. 1 is a view showing a configuration of an automatic urine disposal apparatus of this embodiment.

At least the following matters will become apparent with the following description taken in connection with the accompanying drawings.

A defecation detection apparatus including: a feces/urine receiving member that is placed to face the body of a wearer and that receives discharged feces and urine; a urine suction device that is detachably attached to the feces/urine receiving member and that can suck urine discharged in the feces/urine receiving member; a temperature sensor that is placed at a defecation position where discharged feces are received in the feces/urine receiving member; and a control section that detects the presence of discharged feces based on a signal remaining after removing a signal that is output from the temperature sensor within a predetermined time after an operation of the urine suction device from a signal that is output from the temperature sensor.

In the above defecation detection apparatus, the presence of discharged feces is detected based on the signal remaining after removing the signal that is output from the temperature sensor within the predetermined time after the operation of the urine suction device from the signal that is output from the temperature sensor. Therefore, the determination of the presence of discharged feces is not affected by the temperature change which is caused by the operation of the urine suction device. This enables correct detecting of the presence of discharged feces.

In such a defecation detection apparatus, it is desirable that the apparatus further comprises a urine detection section that detects urine discharged in the feces/urine receiving member, and when the urine detection section detects urine, the control section operates the urine suction device and the urine suction device sucks the urine in the feces/urine receiving member.

In the above defecation detection apparatus, since the urine suction device is operated when the urine detection section has detected discharge of urine, the wearer can continue to wear the feces/urine receiving member comfortably. At this stage, the presence of feces is detected based on the signal remaining after removing the signal that is output from the temperature sensor within the predetermined time after the operation of the urine suction device from the signal that is output from the temperature sensor. Therefore, though the apparatus includes the urine suction device, the apparatus can detect correctly the presence of feces.

In such a defecation detection apparatus, it is desirable that the control section operates the urine suction device periodically.

In the above defecation detection apparatus, while the urine suction device is periodically operated, the presence of feces is detected based on the signal remaining after removing the signal that is output from the temperature sensor within the predetermined time after the operation of the urine suction device from the signal that is output from the temperature sensor. Therefore, it is possible to detect the presence of discharged feces correctly while operating the urine suction device periodically.

In such a defecation detection apparatus, it is desirable that when an absolute temperature detected by the temperature sensor is lower than a predetermined temperature, the control section does not detect the presence of discharged feces.

When the urine suction device is operated, the signal output from the temperature sensor changes significantly. If the determination is made based on a temperature change as measured with respect to temperature which has dropped significantly, the possibility of erroneous determination will be high. Therefore, when the absolute temperature detected by the temperature sensor is lower than a predetermined temperature, erroneous detection can be prevented or reduced by performing no detection of the presence of discharged feces.

In such a defecation detection apparatus, it is desirable that the predetermined temperature is a temperature of a human body.

The temperature of discharged feces is higher than the temperature of a human body. Therefore, when the absolute temperature detected by the temperature sensor is lower than the temperature of a human body, erroneous detection can be further prevented or reduced by performing no detection of the presence of discharged feces.

In such a defecation detection apparatus, it is desirable that based on a rate at which a temperature falls after detecting a rise of the temperature by the signal that is output from the temperature sensor, the control section determines whether at least one of urine and feces has been discharged.

Feces and urine have a higher temperature than the body temperature at the time of discharge. However, feces and urine are different in the way the temperature falls over time after discharge, that is, in the rate at which the temperature falls, because of the difference in heat capacity. Therefore, as in the defecation detection apparatus described above, the control section determines that at least one of urine and feces has been discharged, based on the rate at which the temperature falls after the detection of a rise of the temperature by the signal that is output from the temperature sensor placed in the feces/urine receiving member. This makes it possible to more correctly determine whether it is urine or feces that have been discharged.

In such a defecation detection apparatus, it is desirable that after determining that feces has been discharged, the control section detects an amount of the temperature rise based on the signal that is output from the temperature sensor, and determines whether an amount of the discharged feces is large or small, using the rise amount.

In the signal output from the temperature sensor, the detected temperature varies depending on the amount of discharged feces. For example, if the amount of feces is large, the detected temperature is high because the entire temperature sensor is covered with feces. On the other hand, if the amount of feces is small, the detected temperature is lower compared with the case of the large feces amount. This is because the temperature sensor is covered partly, or not covered at all, with feces. Therefore, as with the abovementioned defecation detection apparatus, the following steps after determining that feces has been discharged make it possible to determine, not only the presence of discharged feces, but also whether the amount of discharged feces is large or small: first detecting the temperature-rise amount based on the signal that is output from the temperature sensor; and then determining whether the discharged amount is large or small using the detected rise amount.

In such a defecation detection apparatus, it is desirable that the temperature sensor is covered with a sheet material, and a temperature of feces is detected over the sheet material.

In the above defecation detection apparatus, since discharged feces do not come into direct contact with the temperature sensor, the signal that is output from the temperature sensor easily changes depending on the amount of discharged feces. Therefore, it is possible to determine more correctly whether the amount of discharged feces is large or small.

Moreover, since the sheet material placed between the temperature sensor and feces is a nonwoven fabric, an air space is formed therebetween. Therefore, when the amount of discharged feces is large, the air space is pressed down under the weight of the feces, permitting the temperature to be detected at a position where the temperature sensor is closer to the feces. On the other hand, when the amount of discharged feces is small, the temperature of the feces is detected over the air space. This makes it possible to detect more correctly whether the amount of discharged feces is large or small.

In such a defecation detection apparatus, it is desirable that the apparatus further comprises a first temperature sensor that is placed at a defecation position in the feces/urine receiving member where discharged feces are received, and a second temperature sensor that is placed at a non-defecation position in the feces/urine receiving member where discharged feces are not received, and the control section determines whether it is urine or feces that has been discharged, based on data remaining after a signal that is output from the second temperature sensor has been removed from a signal that is output from the first temperature sensor.

In the above defecation detection apparatus, the first temperature sensor is placed at the defecation position of the feces/urine receiving member. Therefore, the first temperature sensor is close to feces when the feces are discharged, which causes a rapid rise of the temperature. On the other hand, the second temperature sensor is placed at a non-defecation position of the feces/urine receiving member. Therefore, the second temperature sensor is away from feces when discharged, which does not cause rapid rise of the temperature due to the discharged feces. Moreover, since the first and second temperature sensors are placed on the single feces/urine receiving member, the sensors undergo almost the same influence of a temperature change in the space between the feces/urine receiving member and the body, the temperature change being caused by other than defecation. Thus, the control section determines that at least one of urine and feces has been discharged, based on the signal remaining after the signal that is output by the second temperature sensor has been removed from the signal that is output by the first temperature sensor, the signal from the second sensor including a temperature change caused by other than defecation, the signal from the first sensor including a temperature change due to defecation and a temperature change caused by other than defecation. This makes it possible to determine more correctly that at least one of urine and feces has been discharged. The defecation position as used herein refers to a certain position within the feces/urine receiving member at which the feces collects when a person who is bedridden and requires care wears the feces/urine receiving member and discharges feces. More specifically, the defecation position corresponds to an area including a position facing the anus of the bedridden person and a position on the side closer to the back with respect to the anus. The non-defecation position as used herein refers to a position of the feces/urine receiving member other than the defecation position, for example.

In such a defecation detection apparatus, it is desirable that the second temperature sensor is placed at a position facing the groin when the feces/urine receiving member faces the body or at a position between the position facing the groin and the defecation position.

In the above defecation detection apparatus, since persons who need defecation detection are those who require nursing care such as bedridden elderly persons, for example, the defecation determination apparatus is used for such persons requiring care when lying on the bed. When a person requiring care discharges feces when lying on the bed, the feces will collect at a position lower than his or her body, that is, at a position on the back side of the body. In addition, it is desirable that the second temperature sensor capable of detecting a temperature change caused by other than defecation be placed at a position in the non-defecation position which is as close to the first temperature sensor as possible and will not be covered with feces. Therefore, by placing the second temperature sensor at a position facing the groin or a position between the position facing the groin and the defecation position, the second temperature sensor can be prevented from being covered with feces and can more reliably detect a temperature change caused by other than defecation in the first temperature sensor. This makes it possible to detect more correctly whether either feces or urine has been discharged.

In such a defecation detection apparatus, it is desirable that the first temperature sensor and the second temperature sensor are formed on a single insulating synthetic resin film.

In the above defecation detection apparatus, the first and second temperature sensors are formed on the single insulating synthetic resin film. Therefore, the sensors can be easily attached to the film without the necessity of attaching the first sensor and the second sensor separately. Also, the first and second temperature sensors are formed on the insulating synthetic resin film, which is thin and flexible. Therefore, the user can use the apparatus without discomfort.

In such a defecation detection apparatus, it is desirable that the apparatus further comprises a notification section that notifies that feces has been discharged, and when it is determined that feces has been discharged, the control section operates the notification section.

In the above defecation detection apparatus, when defecation is determined, it is possible to give notification of the defecation to the caregiver, for example.

In such a defecation detection apparatus, it is desirable that the control section does not operate the notification section when it is determined that an amount of the discharged feces is smaller than a predetermined amount.

If the notification section is operated when feces is discharged but the discharged amount is too small to require replacement of the feces/urine receiving member, the caregiver will have to replace the feces/urine receiving member when actually replacement is unnecessary. With the defecation detection apparatus described above, the notification section is not operated when the amount of feces is too small to require replacement of the feces/urine receiving member. This makes it possible to reduce the burden on the caregiver, etc.

In such a defecation detection apparatus, it is desirable that the urine detection section is a pair of electrodes formed on the insulating synthetic resin film with spacing therebetween, and discharge of urine is detected based on a change in voltage between the pair of electrodes, the change being caused by discharged urine.

In the above defecation detection apparatus, since the urine detection section includes the pair of electrodes formed on the insulating synthetic resin film with spacing therebetween, it is possible to provide the urine detection section at low cost. Also, since the pair of electrodes are formed on the thin, flexible insulating synthetic resin film, the user can use the apparatus without discomfort. Moreover, the presence of urine increases the conductivity of the pair of electrodes with spacing therebetween. This makes it possible to more reliably detect urine by detecting urine based on a change in the voltage between the electrodes.

Configuration of Automatic Urine Disposal Apparatus

An automatic urine disposal apparatus as an example of the defecation detection apparatus will be described with reference to the accompanying drawings.

FIG. 1 is a view showing a configuration of an automatic urine disposal apparatus 100 of this embodiment. The automatic urine disposal apparatus 100 includes: a urine absorption member 102 shown as a partly cutaway figure; and a controller 101 provided with a vacuum suction device 100a as a urine suction device. To the controller 101 the urine absorption member 102 is attached detachably. The urine absorption member 102 has an inner-surface side facing the skin of a wearer (not shown) and an outer-surface side opposite to the inner-surface side facing the clothing of the wearer. The urine absorption member 102 is worn together with a pair of pants 300 to allow the inner surface to be in close contact with the skin; the pants 300 serve as the clothing and are shown by phantom lines in FIG. 1. The pants 300 have a front waist region 301, a back waist region 302, and a crotch region 303, and are preferably made of, for example, a meshed cloth so that the outer-surface side can be easily seen through the pants. Note that the urine absorption member 102 can be worn with, not only the pants 300 as illustrated, but also other appropriate members such as an open diaper secured with tapes, a pull-on diaper, a diaper cover, pants for incontinence patients, etc.

The automatic urine disposal apparatus 100 is an apparatus that can collect urine discharged by the wearer in the urine absorption member 102 and dispose of the collected urine. The urine absorption member 102 has a container section 102a and a detection section 150. The container section 102a faces the skin of the wearer near the urethral opening and can receive discharged urine. The detection section 150 includes: a urine detection section 102b that detects discharge of urine; and thermistors 145 as a feces detection section that detects feces (see FIG. 5). The vacuum suction device 100a includes: a joint member 104 for connection to the container section 102a; a urine guide tube 106; a urine tank 106a; a pump unit 108; electrical wiring 116; and the like.

The pump unit 108 includes: a control circuit 108a as a control section that processes electric signals sent from the detection section 150 via the electrical wiring 116; a suction pump 108b the drive of which is controlled by the control circuit 108a; and the like. In the urine absorption member 102, the urine guide tube 106 is connected via the joint member 104 to a urine drainage port 114 formed on the peripheral wall of a container 112 of the container section 102a. A clip 120 is attached to the end of the electrical wiring 116 extending from the pump unit 108. The clip 120 is for electrically connecting the electrical wiring 116 to urine detection electrodes 218a and 218b (see FIG. 5) and to power supply electrodes 143a, 143b, and 143c; the urine detection electrodes 218a and 218b are a pair of electrodes constituting the urine detection section 102b of the detection section 150, and the power supply electrodes 143a, 143b, and 143c supply power to the thermistors 145.

In such an automatic urine disposal apparatus 100, when urine is discharged, a detection signal is sent from the urine detection section 102b to the pump unit 108, which then actuates the suction pump 108b to suck the air in the urine tank 106a, thereby sucking the urine into the container 112 and further sucking the urine in the container 112 via the joint member 104 and the urine guide tube 106, to be collected in the urine tank 106a. In addition, signals output from the thermistors 145 placed in the urine absorption member 102 are sent to the pump unit 108. The control circuit 108a of the pump unit 108 allows an alarm lamp 504 as a notification section to blink based on the received signals, thereby notifying a caregiver of the presence of feces.

With the suction by the suction pump 108b, urine are sucked and also the air between the urine absorption member 102 and the body are sucked. The automatic urine disposal apparatus 100 actuates the suction pump 108b periodically irrespective of detection of urination, for example, every hour, to ventilate the space between the urine absorption member 102 and the body.

As shown in FIG. 1, when the urine absorption member 102 is worn, the clip 120 is on the belly side. The urine absorption member 102 is worn in the following manner: most of the container 112 of the urine absorption member 102 extends in the vertical direction on the front side of the wearer's body; the inside thereof faces the urethral opening and its surrounding skin of the wearer; and the lower end portion extends while curving gradually along the inner surface of the crotch region 303 toward the anus to reach the back of the body. In particular, since the urine absorption member 102 is preferably worn by a bedridden person, the urine absorption member 102 is formed located on a portion of the crotch region 303 closer to the back waist region 302. Therefore, the urine absorption member 102 can receive not only urine but also discharged feces.

Figure 2:
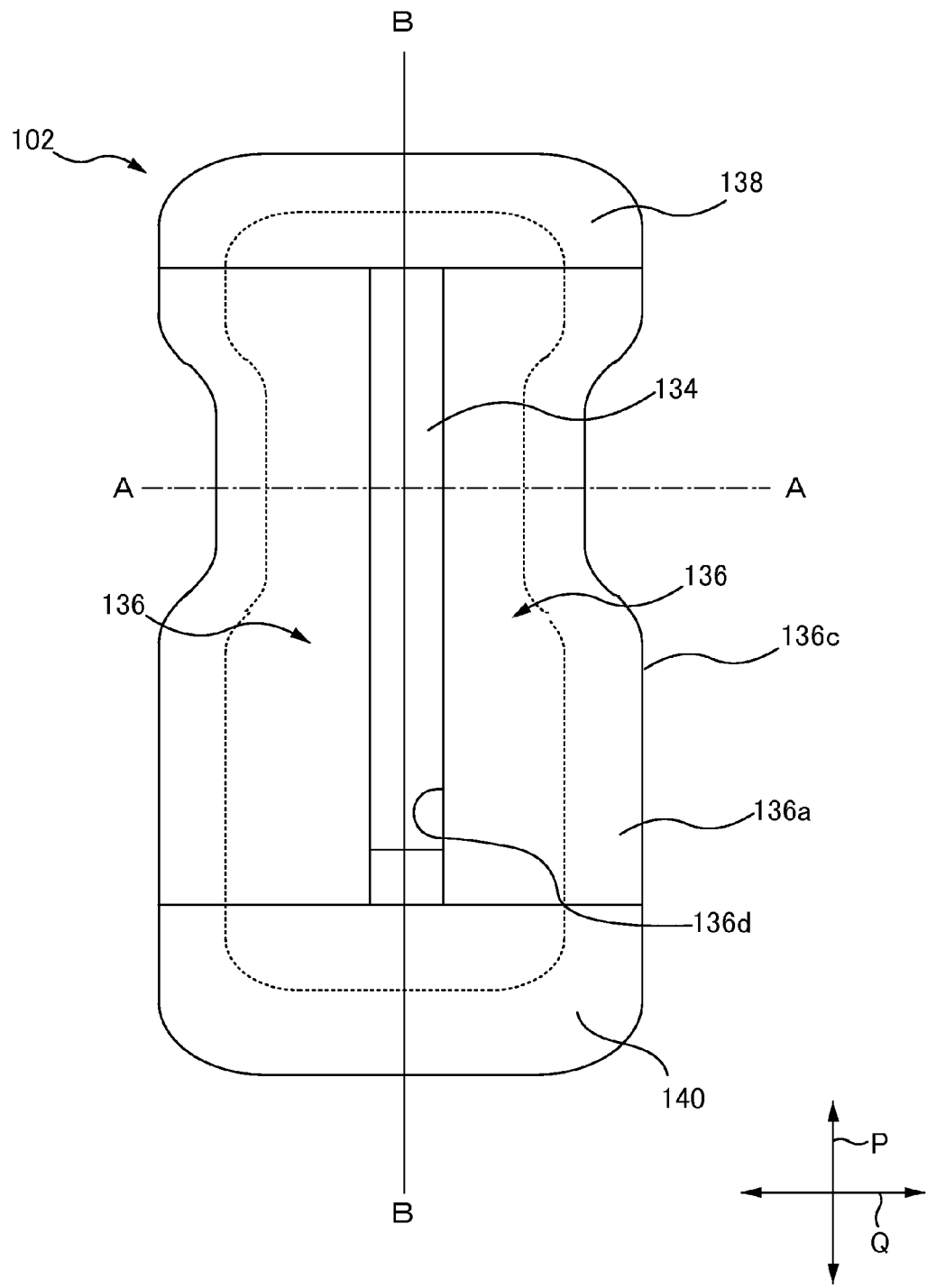
FIG. 2 is a plan view showing the inner side of a urine absorption member.
Figure 3:
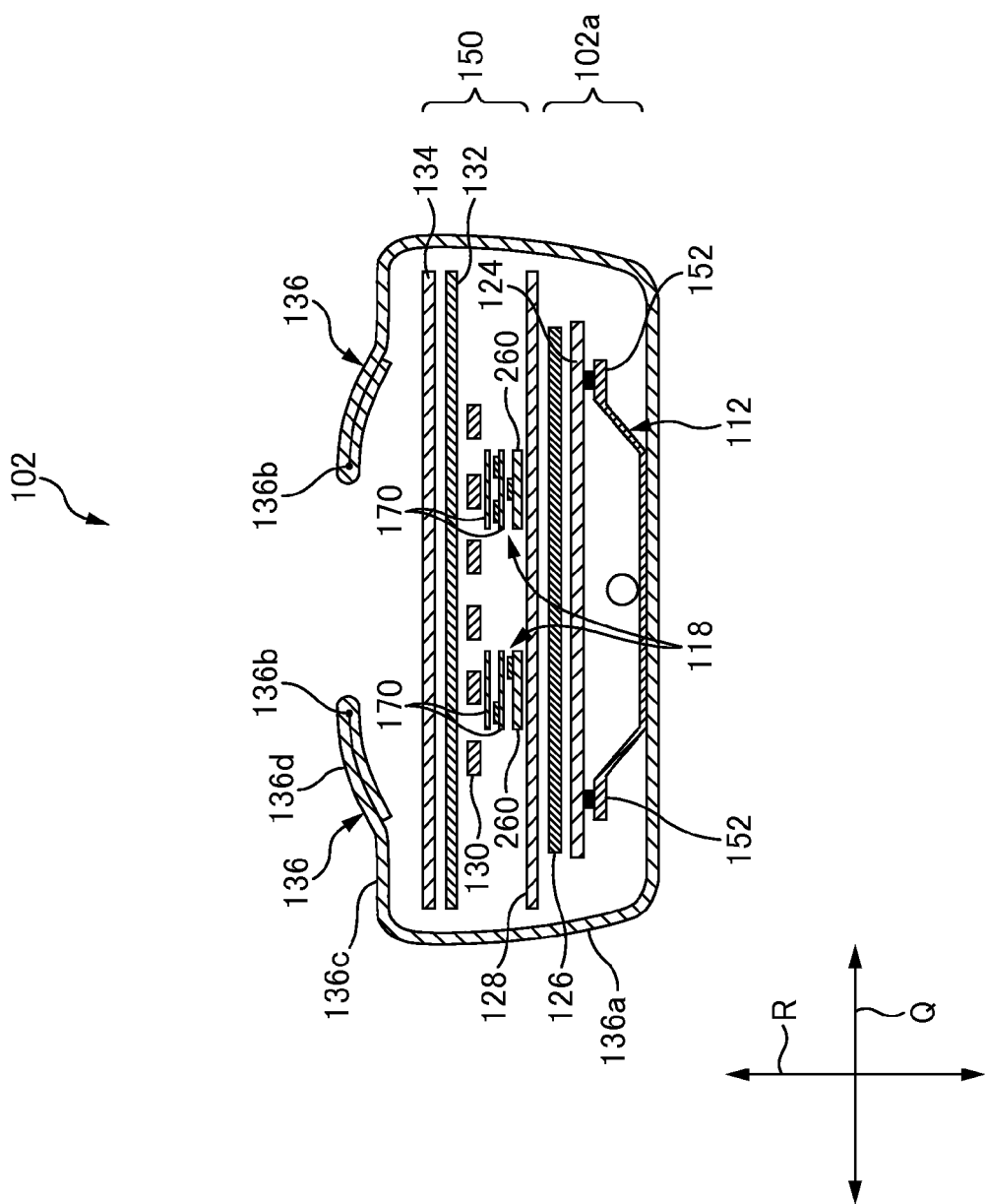
FIG. 3 is a view showing a section taken along line A-A in FIG. 2.
Figure 4:
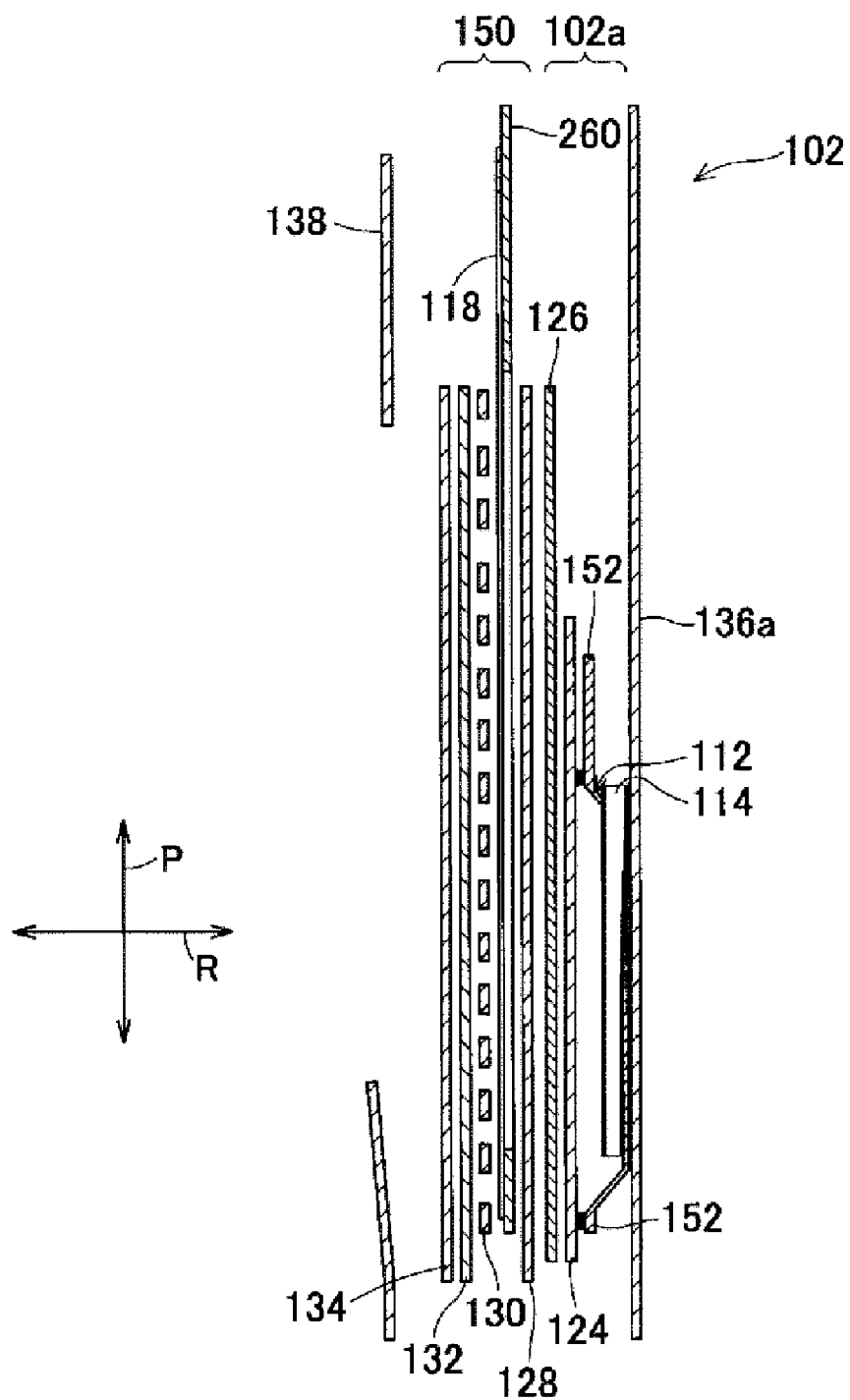
FIG. 4 is a view showing a section taken along line B-B in FIG. 2.

FIG. 2 is a plan view showing the inner-surface side of the urine absorption member 102, FIG. 3 is a view showing a section taken along line A-A in FIG. 2, and FIG. 4 is a view showing a section taken along line B-B in FIG. 2. Note that, in FIGS. 3 and 4, components which should be placed one upon another in the thickness direction R of the urine absorption member 102 are shown as if they are apart from one another with some exceptions. The thickness direction R is also the direction of the depth of the container section 102a.

The urine absorption member 102 has the length direction P which is aligned with the front-back direction of the wearer's body and the width direction Q orthogonal to the length direction P; the urine absorption member 102 is wide in portions at and near both ends in the length direction P and is narrow in the center portion. The urine absorption member 102 also has the thickness direction R. On the upper side of the container 112 as viewed from FIG. 3 (the skin side when worn), there are placed, one upon another, a plurality of sheet-like members including: a liquid-permeable, low-air-permeable sheet 124; a diffusion sheet 126; a cushion sheet 128; an electrode unit 118; a spacer 130; a filter 132; and a liquid-permeable, skin-contact sheet 134, in this order from the bottom side (the clothing side when worn) upward in the thickness direction R. The skin-contact sheet 134 corresponds to a sheet material. A pair of leakage barriers 136 lie on the skin-contact sheet 134. The low-air-permeable sheet 124 and the diffusion sheet 126 are integrated with the container 112, to form the container section 102a. The cushion sheet 128, the electrode unit 118, the spacer 130, the filter 132, and the skin-contact sheet 134 lie one upon another, to form the detection section 150. In this embodiment, the portion of the urine absorption member 102 excluding the electrode unit 118 corresponds to the feces/urine receiving member for receiving feces and urine.

The container 112, in the shape of a tray, is formed of a flexible, elastic member such as a flexible polyethylene and silicone rubber and has a flexibility permitting bending both in the length direction P and the width direction Q, but is built to resist deformation due to a negative pressure created when the suction pump 108b sucks urine. The low-air-permeable sheet 124 is bonded to a peripheral flange 152 of the container 112 at a position 112a by adhesion or welding. The depth direction of the container 112 is the same as the thickness direction R.

The low-air-permeable sheet 124, which is highly permeable to liquid but has low permeability to air or is impermeable to air, covers the top opening of the container 112. Inside the container 112 having the low-air-permeable sheet 124, a negative pressure is easily created when the suction pump 108b of the pump unit 108 is actuated, permitting prompt suction of urine. As the low-air-permeable sheet 124, it is possible to use an SMS nonwoven fabric formed of a 22 g/m$^2$ spunbonded nonwoven fabric, a 10 g/m$^2$ melt-blown nonwoven fabric, and a 22 g/m$^2$ spunbonded nonwoven fabric, preferably subjected to hydrophilic treatment with a surfactant. The air permeability of the low-air-permeable sheet 124 as measured according to method A of the air permeability measurement methods defined in JIS L 1096 6.27.1 is in the range of 0 to 100 cc/cm$^2$/sec., preferably in the range of 0 to 50 cc/cm$^2$/sec., in its wet state. And, in its dry state, the air permeability is in the range of 20 to 200 cc/cm$^2$/sec., preferably in the range of 20 to 100 cc/cm$^2$/sec., more preferably in the range of 20 to 50 cc/cm$^2$/sec. The wet state at the measurement of the air permeability is defined as the state where the water content of the low-air-permeable sheet 124 below is 100% or more as calculated in equation (1). And, the dry state is defined as the state of the low-air-permeable sheet 124 observed after having been left to stand in a 20° C., 50% RH room for 24 hours or more.

Water content=(wet-state sheet weight−dry-state sheet weight)/(dry-state sheet weight)  (1)

The diffusion sheet 126 is formed of a liquid-permeable sheet piece such as a nonwoven fabric including hydrophilic fibers such as rayon fibers, for example. The diffusion sheet 126 is used for putting the low-air-permeable sheet 124 into a wet state over a wide area, when urine is discharged, by promptly diffusing the urine over the surface (skin side) of the low-air-permeable sheet 124. With the low-air-permeable sheet 124 being in the wet state, it is easy to suck the urine into the container 112 by creating a negative pressure in the container 112. It is preferable that the diffusion sheet 126 be bonded to the low-air-permeable sheet 124 intermittently so as not to impair the liquid permeability of either.

The cushion sheet 128 is formed of a liquid-permeable sheet piece such as a thermal bonded nonwoven fabric having a basis weight of 20 to 30 g/m$^2$, for example. The cushion sheet 128 allows urine to permeate therethrough promptly, and prevents backflow of urine present in the diffusion sheet 126 and the low-air-permeable sheet 124 to the electrode unit 118. Also, by placing the sheet-like members such as the electrode unit 118, the spacer 130, the filter 132, etc. on the cushion sheet 128, the cushion sheet 128 serves as a carrier member in the process of manufacturing the urine absorption member 102, the carrier member being for placing these sheet-like members at a predetermined position in the urine absorption member 102. It is preferable that the cushion sheet 128 be bonded to the diffusion sheet 126 intermittently so as not to impair the liquid permeability of either.

The electrode unit 118 has thin-film thermistors (hereinafter simply referred to as thermistors) mounted thereon, which are for detecting feces. The electrode unit 118 includes the following electrodes printed on a synthetic resin film with conductive ink: electrodes in a predetermined shape for detecting urine; and electrodes for supplying electric power to the thermistors. The details of the electrode unit 118 will be described later. The electrode unit 118 can be bonded to the cushion sheet 128. As the thermistors 145 suitable for the automatic urine disposal apparatus 100, thermistors which are small in heat capacity and susceptible to the surrounding temperature are preferable. An example of such thermistors is thermistors ET-103 manufactured by Ishizuka Electronics Corporation.

The spacer 130 is thickest among the sheet-like members of the detection section 150, and is formed of a net-shaped liquid-permeable sheet piece. In the urine absorption member 102, some urine may remain in the skin-contact sheet 134 after suction of urine, which results in leaving the skin-contact sheet 134 in the wet state with the remaining urine. Such a skin-contact sheet 134 may cause a malfunction of the automatic urine disposal apparatus 100 by coming into contact with the electrode unit 118 directly or indirectly under the action of the pressure from the body, etc. The spacer 130 is a member provided to secure spacing between the electrode unit 118 and the filter 132 in the thickness direction R, thereby preventing such a malfunction. The spacer 130 has water repellency but no urine absorption capability, and has air permeability and liquid permeability higher than the low-air-permeable sheet 124, and does not change in thickness under the pressure from the body. Such a spacer 130 can be formed of a net having a thickness of 0.5 to 1 mm made of a flexible synthetic resin such as ethylene-vinyl acetate, and is preferably bonded to the cushion sheet 128 so as not to impair the liquid permeability of either.

The filter 132 is provided to prevent occurrence of an event that a solid content included in urine may attach to the electrode unit 118 causing the electrode unit 118 to permanently carry a current. The filter 132 is formed of a sheet piece, more preferably a nonwoven fabric, having air permeability and liquid permeability higher than the low-air-permeable sheet 124. The filter 132 can be bonded to the spacer 130 so as not to impair the liquid permeability of either.

The skin-contact sheet 134 is placed on the surface (skin side) of the filter 132. The skin-contact sheet 134, when the urine absorption member 102 is worn, comes into contact with the wearer's skin while facing the urethral opening and its surrounding skin of the wearer. Such a skin-contact sheet 134 is formed of a sheet piece having flexibility and liquid permeability, such as a thermal bonded nonwoven fabric having a basis weight of 15 to 25 g/m$^2$, for example. Like the cushion sheet 128, the skin-contact sheet 134 allows urine to permeate therethrough instantaneously at the initial stage of urination, and is preferably bonded to the filter 132 intermittently so as not to impair the liquid permeability of either. The skin-contact sheet 134 may be hydrophilic in some cases and water-repellent in other cases.

The pair of leakage barriers 136 are placed on the right and left sides as shown in FIGS. 2 and 3, and can prevent urine from flowing on the skin-contact sheet 134 in the width direction Q and leaking sideways from the urine absorption member 102. In the leakage barriers 136 shown in FIG. 3, outer edge portions 136c located on the outer side of the urine absorption member 102 are bonded to the skin-contact sheet 134. On the other hand, inner edge portions 136d located on the inner side of the urine absorption member 102 are not bonded to the skin-contact sheet 134. But, to the inner edge portions 136d, elastic members 136b such as rubber threads are attached in the stretched state in the length direction P. A sheet 136a constituting the pair of leakage barriers 136 covers the bottom of the container 112. When being worn, the urine absorption member 102 bends in the length direction P as shown in FIG. 1, causing the elastic members 136b to shrink. As a result, the inner edge portions 136d of the leakage barriers 136 stand upward away from the skin-contact sheet 134. It is preferable that the sheet 136a forming the leakage barriers 136 be liquid impermeable. For this purpose, a flexible thermoplastic synthetic resin film, a composite sheet of this film and a nonwoven fabric, etc. can be used. In the plan view of the urine absorption member 102 (see FIG. 2), the top and bottom end portions of the leakage barriers 136 are covered with first and second end sheets 138 and 140, respectively.

Figure 5:
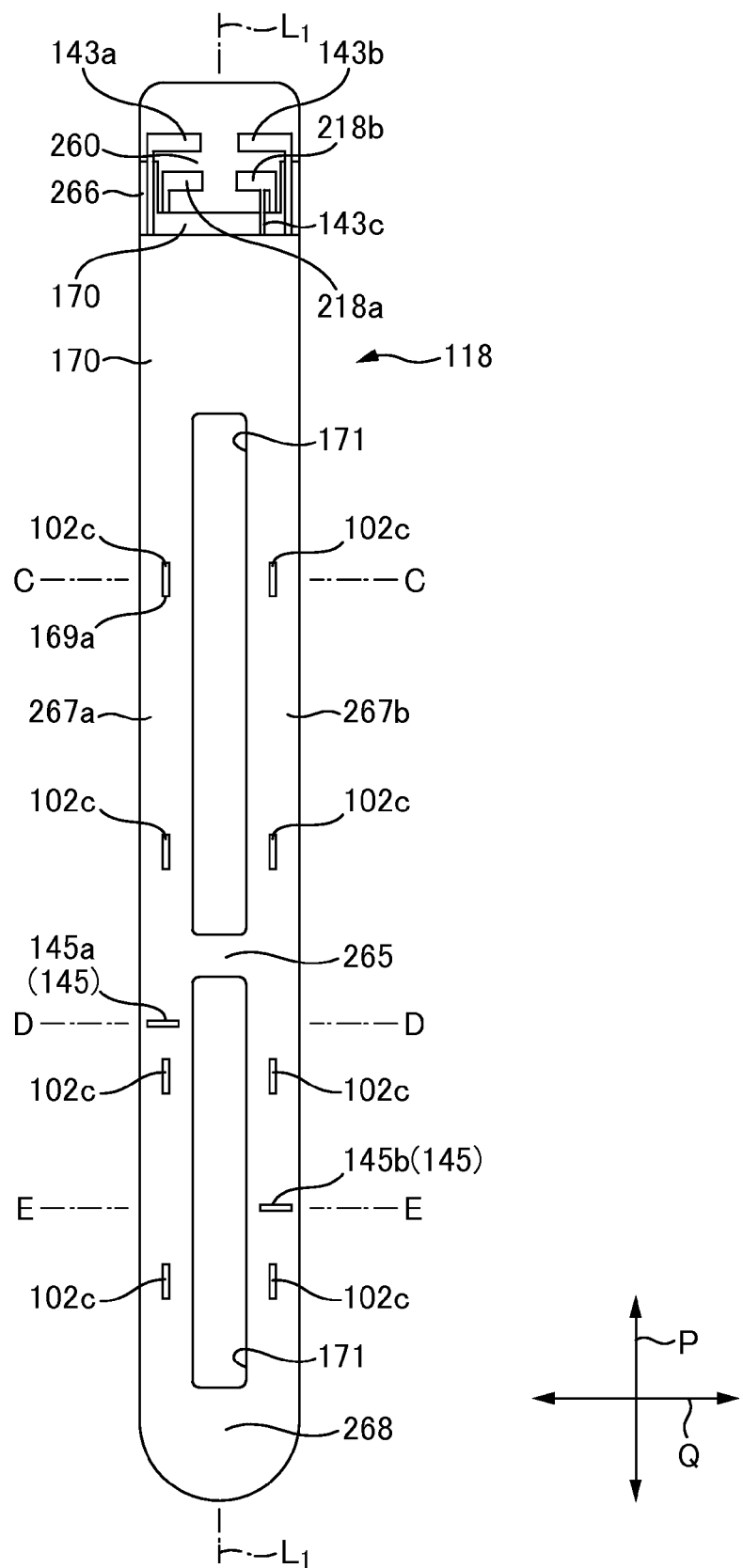
FIG. 5 is a plan view of an electrode unit.

FIG. 5 is a plan view of the electrode unit 118 shown in FIGS. 2, 3, and 4. The electrode unit 118 includes: an insulating film 260 formed of a synthetic resin film; the pair of urine detection electrodes 218a and 218b formed on one surface of the film 260; two thermistors and the power supply electrodes 143a, 143b, and 143c for supplying power to the thermistors; and an insulating coating 170 covering most of these electrodes 218a, 218b, 143a, 143b, and 143c. The thermistors and the power supply electrodes are formed on the same surface of the film 260 as the urine detection electrodes are.

The film 260, in the shape of a strip extending in the length direction P, has two rectangular openings 171; the openings 171 are elongated in the length direction P and are formed by cutting out central portions of the film 260 in the width direction Q. Such a film 260 has: a top end portion 266 in the upper part of FIG. 5; side portions 267a and 267b below the top end portion 266; and a bottom end portion 268 and a connecting portion 265 in the lower part. The top end portion 266 is for being gripped with the clip 120. The side portions 267a and 267b are located on both sides of the center line L1-L1 bisecting the width of the electrode unit 118. The bottom end portion 268 continues from the side portions 267a and 267b. The connecting portion 265 connects the side portions 267a and 267b to each other at a position between the top end portion 266 and the bottom end portion 268. On the top end portion 266 of the film 260, the ends of the urine detection electrodes 218a and 218b and the ends of the power supply electrodes 143a, 143b, and 143c are exposed. Also, the insulating coating 170 has eight uncoated portions 169a on the side portions 267a and 267b. Such uncoated portions 169a are arranged in two lines in the length direction P at appropriate intervals with two each aligned in the width direction Q. The urine detection electrodes 218a and 218b are partly exposed from the uncoated portions 169a to allow the electrodes 218a and 218b to get wet with urine.

More specifically, the urine detection electrodes 218a and 218b are formed on one surface of the film 260, extending from the top end portion 266 to the bottom end portion 268 through the side portions 267a and 267b. Such urine detection electrodes 218a and 218b then turn on the bottom end portion 268 inwardly in the width direction Q, extend upward along the opening 171 closer to the bottom end portion 268, and are connected to each other on the connecting portion 265. The portions of the urine detection electrodes 218a and 218b from the turning section on the bottom end portion 268 to the connection on the connecting portion 265 serve as a break detection circuit 250 to be described later. The urine detection electrodes 218a and 218b are covered with the insulating coating 170 except for the uncoated portions 169a and the ends on the top end portion 266, the ends being connected to the pump unit 108 when gripped with the clip 120.

On the surface side of the insulating coating 170, the power supply electrodes 143a, 143b, and 143c are formed extending from the top end portion 266 through the side portions 267a and 267b. The ends of the power supply electrodes 143a and 143b are located closer to the top end portion than the urine detection electrodes 218a and 218b. In the side portions 267a and 267b, those ends are located on the outer side of the urine detection electrodes 218a and 218b in the width direction of the electrode unit 118. The power supply electrode 143c is formed such that only the top portion thereof overlaps either one of the urine detection electrodes 218a and 218b which are exposed on the top end portion 266. The other portion of the power supply electrode 143c than the top end portion is formed on the insulating coating 170 which is provided on the surface side of the overlapped one of the urine detection electrode 218a or 218b (218b in the illustrated example). And, the other portion of the power supply electrode 143c extends to the side portion 267b on the inner side of the urine detection electrode 218a or 218b, and is split into two branches at the connecting portion 265. One of the branches which is split toward the connecting portion 265 extends straight in the length direction P of the electrode unit 118, and the other extends on the connecting portion 265 and then extends between the urine detection electrode 218a and the opening 171 closer to the bottom end portion 268.

The power supply electrode 143a and the branched portion of the power supply electrode 143c are formed so that, when the urine absorption member 102 is worn, the ends thereof closer to the bottom end portion 268 in the side portion 267a reach a position slightly backward from the groin which corresponds to the center of the urine absorption member 102 in the front-back direction of the wearer's body. The power supply electrode 143b and the straight portion of the power supply electrode 143c are formed so that the ends thereof closer to the bottom end portion 268 reach a position backward from the position facing the anus of the wearer of the urine absorption member 102. The power supply electrodes 143a, 143b, and 143c are covered with the insulating coating 170 excluding the ends on the top end portion 266 and the ends closer to the bottom end portion 268. Note that the portions of the urine detection electrodes 218a and 218b corresponding to the uncoated portions 169a are exposed without being covered with the two-layer insulating coating 170.

The thermistors 145 are placed as follows: extending between the end of the power supply electrode 143a closer to the bottom end portion 268 and the end of the branched portion of the power supply electrode 143c closer to the bottom end portion 268; and extending between the end of the power supply electrode 143b closer to the bottom end portion 268 and the end of the straight portion of the power supply electrode 143c closer to the bottom end portion 268. The surfaces of the thermistors 145 are covered with a protection sheet not shown.

Hereinafter, the thermistor 145 which is located closer to the groin is referred to as a front-side thermistor 145a, and the thermistor 145 which is located closer to the anus is referred to as a back-side thermistor 145b. Also, the position of the front-side thermistor 145a corresponds to a non-defecation position where feces is not received because the position is located higher than the anus when a person requiring care who wears the apparatus lies on his or her back. The position of the back-side thermistor 145b corresponds to a defecation position where feces are received because the position is located lower than the anus. Therefore, the front-side thermistor 145a corresponds to the second temperature sensor, and the back-side thermistor 145b corresponds to the first temperature sensor.

Figure 6:
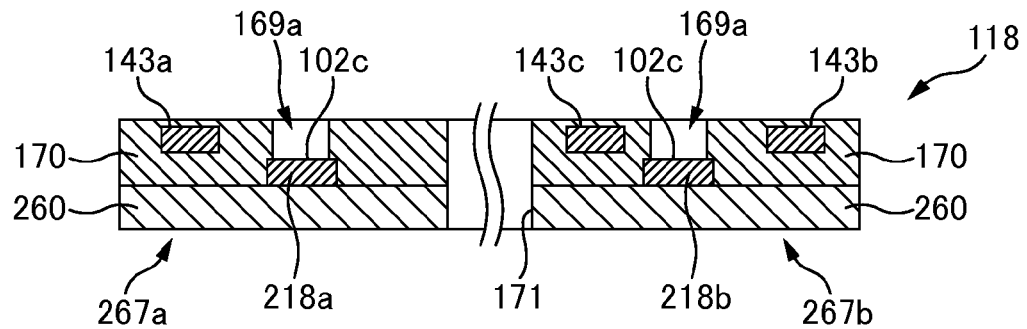
FIG. 6 is a cross-sectional view taken along line C-C in FIG. 5.

FIG. 6 is a cross-sectional view taken along line C-C in FIG. 5, showing exposed portions 102c of the urine detection electrodes 218a and 218b. In FIG. 6, the power supply electrodes 143a, 143b, and 143c are covered with the insulating coating 170.

Figure 7:
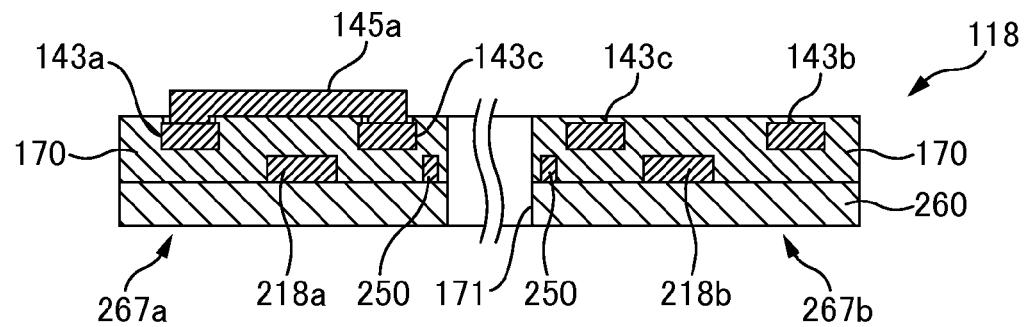
FIG. 7 is a cross-sectional view taken along line D-D in FIG. 5.

FIG. 7 is a cross-sectional view taken along line D-D in FIG. 5, showing how the front-side thermistor 145a is placed. In FIG. 7, the insulating coating 170 covers the following: the break detection circuit 250; the urine detection electrodes 218a and 218b; the power supply electrode 143b; and the power supply electrode 143c on the side portion 267b. The front-side thermistor 145a is connected to the power supply electrode 143a and the power supply electrode 143c on the side portion 267a.

Figure 8:
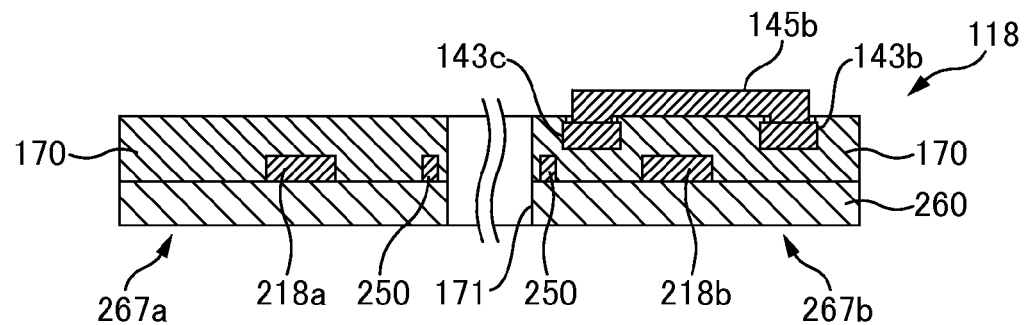
FIG. 8 is a cross-sectional view taken along line E-E in FIG. 5.

FIG. 8 is a cross-sectional view taken along line E-E in FIG. 5, showing how the back-side thermistor 145b is placed. In FIG. 8, the insulating coating 170 covers the break detection circuit 250 and the urine detection electrodes 218a and 218b. The back-side thermistor 145b is connected to the power supply electrode 143b and the power supply electrode 143c on the side portion 267b.

Figure 9:
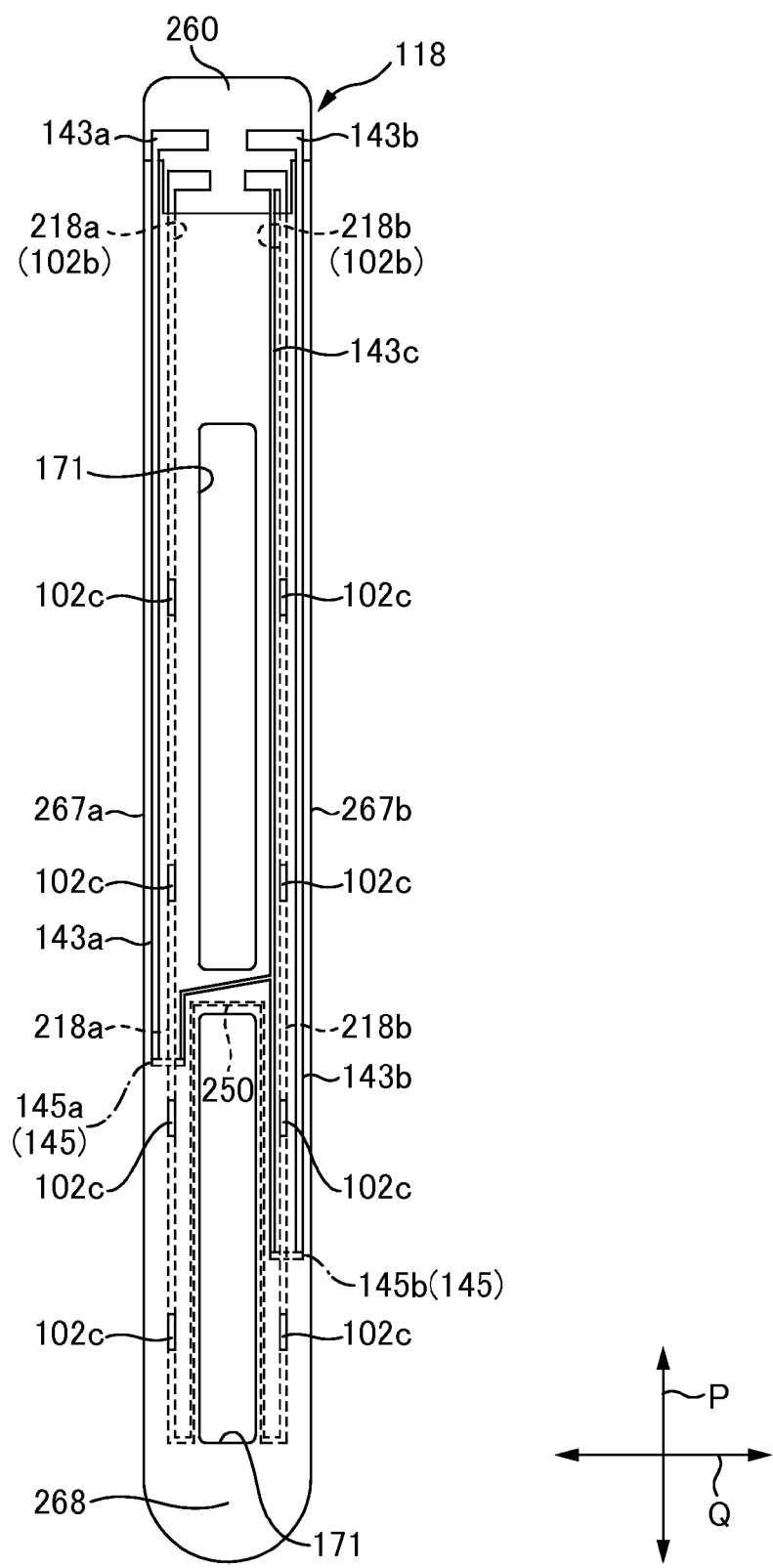
FIG. 9 is a plan view of the electrode unit in a state where an insulating coating is partly removed to expose power supply electrodes.

FIG. 9 is a plan view of the electrode unit 118 in the state where part of the insulating coating 170 is removed to expose the power supply electrodes 143a, 143b, and 143c. On the side portions 267a and 267b of the film 260, the pair of urine detection electrodes 218a and 218b are formed in parallel with spacing therebetween and extend in the length direction P. These urine detection electrodes 218a and 218b are exposed in the uncoated portions 169a in FIG. 5. The break detection circuit 250 is formed between the urine detection electrodes 218a and 218b. The break detection circuit 250 is electrically connected to the bottom end portions of the urine detection electrodes 218a and 218b, and extends along the edge of the opening 171 as illustrated. Also, on the side portions 267a and 267b of the film 260, the power supply electrodes 143a and 143b are formed which are for supplying power to the front-side thermistor 145a and the back-side thermistor 145b. The electrodes 143a and 143b are located on the outer side of the urine detection electrodes 218a and 218b and extend in the length direction P, respectively, with spacing therebetween in the width direction Q. The thermistors 145 are provided at the ends of the power supply electrodes 143a and 143b.

In the electrode unit 118, a polyester film having a thickness of 50 to 100 μm is preferably used as the film 260. The urine detection electrodes 218a and 218b can be formed by printing a required shape on the film 260 using conductive ink, conductive paint and the like. The conductive ink, the conductive paint and the like include the following conductive materials: 3 to 7 wt % of carbon black; 10 to 30 wt % of artificial graphite such as carbon graphite; an appropriate amount of silver powder; and the like, for example. The urine detection electrodes 218a and 218b have a width of 0.5 to 2 mm and a resistance of 150 kΩ or less. The break detection circuit 250 can be formed by printing a required shape on the film 260 using ink including 3 to 7 wt % of carbon black and 5 to 10 wt % of artificial graphite, for example. The break detection circuit 250 has a resistance value much higher than that of the urine detection electrodes 218a and 218b, and is preferably formed to have a width of 0.3 to 1 mm and a resistance value of about 2 to 10 MΩ. The power supply electrodes 143a, 143b, and 143c may be formed with ink and paint similar to those used for the urine detection electrodes 218a and 218b, or may be deposited by vacuum evaporation of aluminum. The power supply electrodes 143a, 143b, and 143c have a width of 0.5 to 2 mm, and at the ends of these power supply electrodes, uncoated portions having an appropriate width are formed where the thermistors 145 are installed.

When the electrode unit 118 and the controller 101 are electrically connected via the clip 120, a very small current is supplied from a power supply 116a (see FIG. 1) of the controller 101 to the urine detection electrodes 218a and 218b. Then, the thermistors 145 are supplied with electric power required to operate the thermistors 145, via the power supply electrodes 143a, 143b, and 143c.

The control circuit 108a of the pump unit 108 continuously or intermittently measures the following: the electric resistance between the urine detection electrodes 218a and 218b or another physical amount equivalent to this electric resistance; and changes in the electric resistances output from the thermistors 145. Note that the urine detection electrodes 218a and 218b are connected to each other via the break detection circuit 250; the control circuit 108a detects a very small current flowing through these electrodes and the circuit. If this current has not been detected within a predetermined time period, it is determined that something unusual has occurred in the urine detection electrodes 218a and 218b, and an alarm is issued to the user of the automatic urine disposal apparatus 100. In addition, the control circuit 108a has a timer (not shown), and the automatic urine disposal apparatus 100 is controlled based on a signal output from the timer. Also, the periodical operation of the suction pump 108b is performed based on the signal output from the timer. The timer is actuated at the time when the automatic urine disposal apparatus 100 is switched on.

When urine is discharged into the urine absorption member 102, the exposed portions 102c of the urine detection electrodes 218a and 218b becomes electrically connected to each other, and the electric resistance between the urine detection electrodes 218a and 218b decreases. Then, the control circuit 108a interprets this decrease as a signal indicating that urine exists in the urine detection section 102b, in other words, that urination is discharged; as a result, the control circuit 108a actuates the suction pump 108b. The degree of decrease of the electric resistance depends on various conditions of the urine absorption member 102, such as the exposed areas of the urine detection electrodes 218a and 218b in the uncoated portions 169a. Therefore, it is possible that the illustrated urine absorption member 102 is set so that the electric resistance between the urine detection electrodes 218a and 218b easily decrease to 0.4 kΩ or less when urine is discharged, and continuation of the electric resistance of 0.4 kΩ or less for a predetermined time, e.g., 0.2 seconds, can be used as the specified resistance value for actuation of the suction pump 108b, that is, the threshold for the same. The suction pump 108b preferably has the capability of completing the suction of urine with the urine absorption member 102 within 1 to 2 minutes. Using such a suction pump 108b, it is possible to determine that something unusual has occurred in the automatic urination apparatus 100 when the operation of the suction pump 108b has continued for three minutes or more, for example.

The thermistors 145a and 145b connected to the control circuit 108a of the pump unit 108 change their electric resistances depending on the temperature of the space between the urine absorption member 102 and the wearer's body. The control circuit 108a detects the electric resistances of the thermistors 145a and 145b at predetermined intervals (e.g., intervals of 1 second). Moreover, the control circuit 108a detects temperature changes in the space between the urine absorption member 102 and the body, by the change per second of the electric resistances based on the detected electric resistances. The front-side thermistor 145a placed at the non-defecation position detects a temperature change at the non-defecation position, and the back-side thermistor 145b placed at the defecation position detects a temperature change at the defecation position.

If the wearer discharges feces and the feces reaches the defecation position, when the feces becomes close to or covers the back-side thermistor 145b, the electric resistance of the back-side thermistor 145b rapidly increases because the temperature of the feces discharged from the body is higher than the body temperature.

The temperatures detected by the front-side thermistor 145a and the back-side thermistor 145b also change at such occasions as the wearer discharges urine and as the wearer moves his or her body. In particular, when the wearer discharges urine, the electric resistance of the back-side thermistor 145b sharply increases, as it does when feces are discharged. It is therefore difficult to detect defecation by only the temperature change which is detected by the back-side thermistor 145b. Therefore, the present inventors have compared the temperature change detected by the back-side thermistor 145b at the time of urination to the temperature change detected by the back-side thermistor 145b at the time of defecation.

Figure 10:
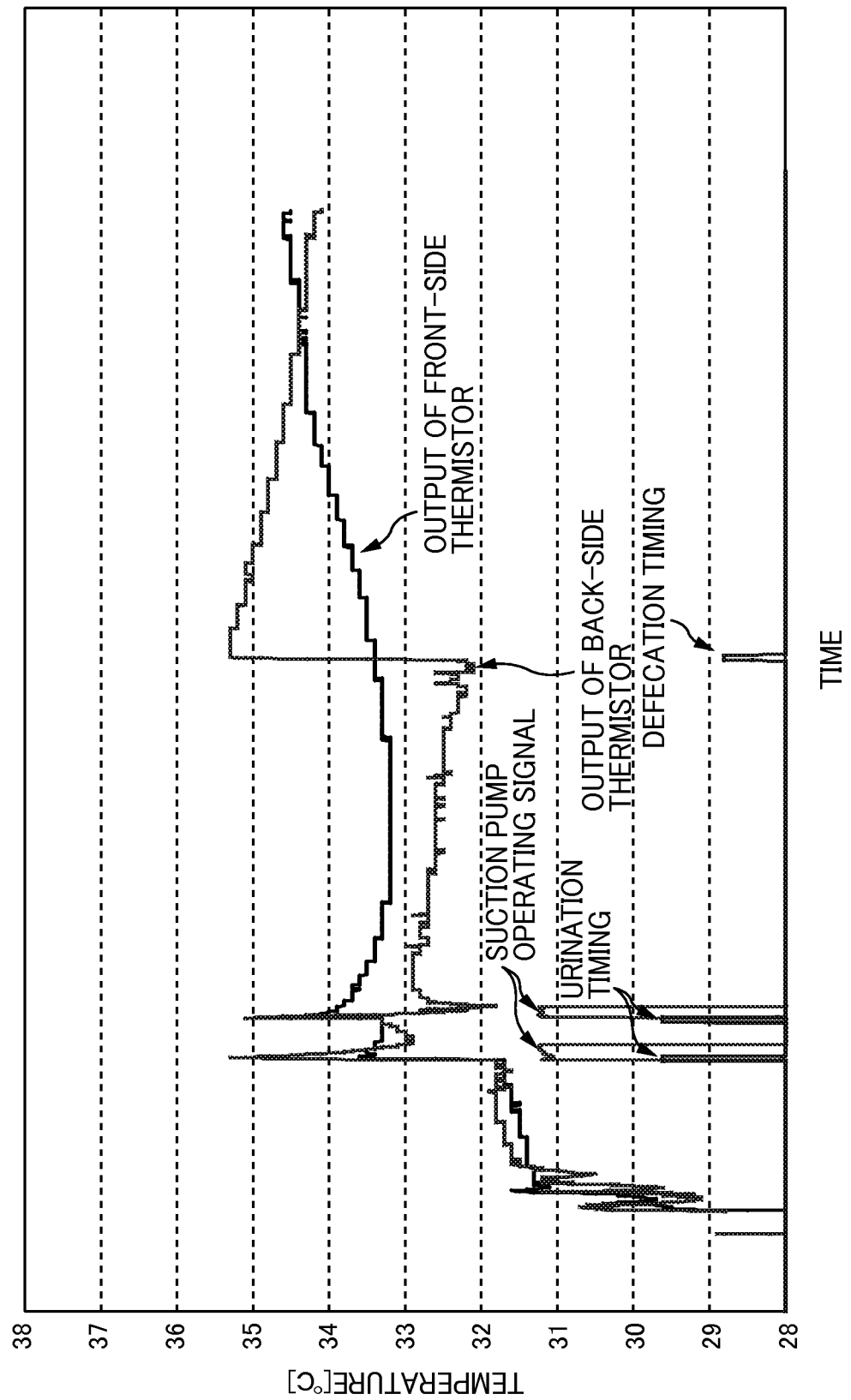
FIG. 10 is a diagram illustrating temperature changes at the time of urination and at the time of defecation.

FIG. 10 is a diagram for explaining the temperature changes at the time of urination and at the time of defecation.

FIG. 10 shows the results of about 1-hour continuous detection of the temperature changes of the front-side thermistor 145a and back-side thermistor 145b of the urine absorption member 102, the urine absorption member 102 being worn by a person who can recognize his or her defecation and urination. When discharging urine or feces, a signal S is input, in order to indicate the discharge, to the control circuit 108a by the wearer's operation. The suction pump 108b is actuated when urination is detected.

As illustrated, the temperature at the time of urination rises by 2 to 3° C. in a few seconds and then falls by about 2° C. in 1 to 2 minutes partly because the suction pump 108b is operating. On the other hand, the temperature at the time of defecation rises by 2 to 3° C. in a few minutes in the same manner as at the time of urination, but then falls only by about 0.3° C. even after the lapse of about 2 minutes. In this way, while the temperature rapidly rises both at the urination and at the defecation, the subsequent temperature change is different: the temperature falls rapidly at the urination, but it falls gradually over time at the defecation. This is probably influenced by the suction of urine by the suction pump 108b, but also seems to be caused by the difference in heat capacity between urine and feces. This difference is highly reliable. Thus, the present inventors have paid attention to the difference in fall of the temperature between the urination and the defecation. In other words, based on the change in the temperature after the rise of the temperature, it is determined that defecation, not urination, has been detected if the fall of the temperature is continuing gradually within the range of a predetermined value (e.g., 1° C.) after a predetermined time (e.g., 2 minutes).

Also, when the amount of discharged feces is large, the feces cover the entire of the surface of the back-side thermistor 145b, causing a rapid temperature rise as described above, and a rise by 2 to 3° C. in a few seconds. However, when the amount of discharged feces is very small, the feces cover partly the surface of the back-side thermistor 145b, or are close to but not in contact with the back-side thermistor 145b. In this state, although the temperature rises, it may fall after a rise of about 1° C. Therefore, when detecting discharge of feces, the control circuit 108a detects the amount of the temperature rise by which the discharge of feces has been detected. And, if the detected rise amount is smaller than a predetermined value (e.g., 1° C.), the control circuit 108a determines that no discharge of feces has been detected. The predetermined value which is the criterion for determination that no discharge of feces has been detected is determined in the following manner: obtaining the amount of the temperature change which is observed when feces is discharged but the discharged amount is too small to require replacement of the urine absorption member 102 by experiments, etc. The obtained temperature change amount is stored in a memory accessible by the control circuit 108a. Based on the information stored in the memory, the control circuit 108a determines whether defecation has occurred or not and whether the alarm lamp 504 should be actuated or not.

In addition, as described above, the temperatures detected by the front-side thermistor 145a and the back-side thermistor 145b also change, for example, when the wearer moves his or her body. Therefore, in order to prevent erroneous detection due to a temperature change which occurs when the body is moved, the automatic urine disposal apparatus 100 is provided with the front-side thermistor 145a. The front-side thermistor 145a, placed at a non-defecation position, is not likely to change its electric resistance due to defecation. And, the front-side thermistor 145a is located at a position relatively near the defecation position and faces the wearer's groin, that is, a non-defecation position. Therefore, for example, when the wearer moves his or her body causing a change in the temperature at a position between the urine absorption member 102 and the body, the output of the front-side thermistor 145a changes and the change is almost the same as the change of the back-side thermistor 145b.

Figure 11:
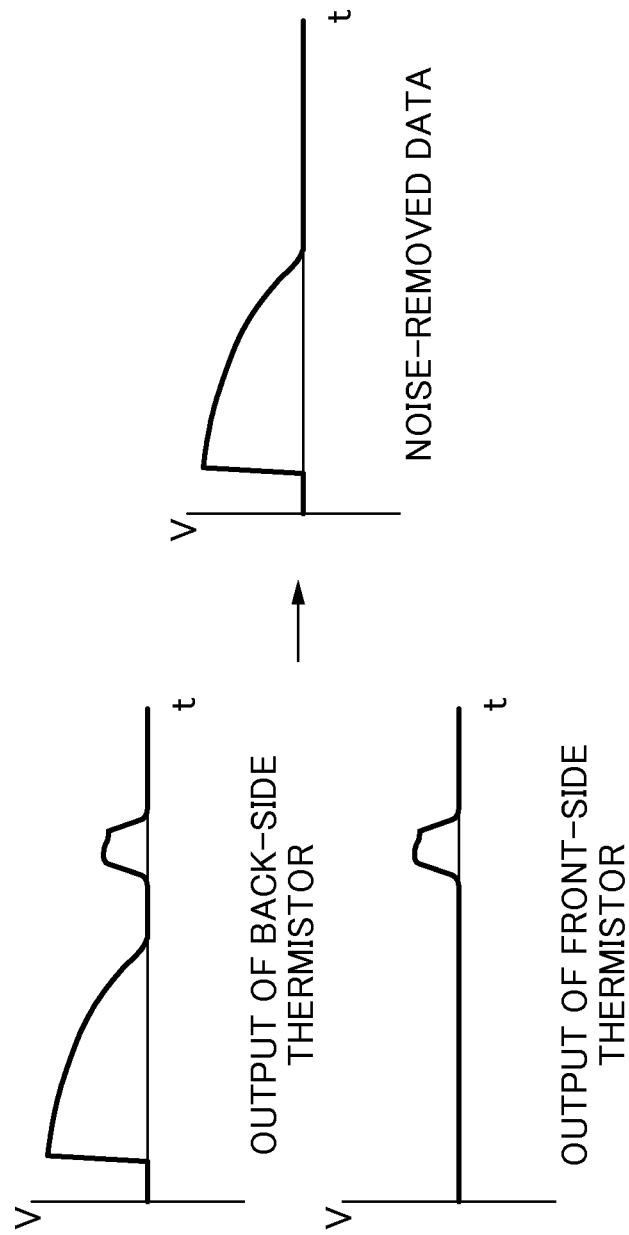
FIG. 11 is a diagram illustrating noise removal processing.

FIG. 11 is a diagram showing temperature changes detected by the front-side thermistor 145a and the back-side thermistor 145b. The upper-left view of FIG. 11 represents the temperature change detected by the back-side thermistor 145b, and the lower-left view of FIG. 11 represents the temperature change detected by the front-side thermistor 145a. In the upper-left view, the signal output from the back-side thermistor 145b indicates that a large temperature rise and fall have occurred in both the first part and the latter part.

In the lower-left view, the signal output from the front-side thermistor 145a indicates that a temperature rise and fall have occurred simultaneously with the latter temperature change in the signal output from the back-side thermistor 145b. In other words, since similar temperature changes have occurred at the defecation position and the non-defecation position in the latter part, it is presumed that the cause of the temperature change in the latter part is not defecation, but is a change in the temperature of the space between the urine absorption member 102 and the body caused by a movement of the wearer's body, etc. Therefore, when detecting defecation based on the temperature of the back-side thermistor 145b, the control circuit 108a first executes noise removal processing of removing the temperature change detected by the front-side thermistor 145a.

The automatic urine disposal apparatus 100 is configured so that the suction pump 108b is actuated at the time of detection of urination and at periodical intervals. When the suction pump 108b is actuated, the temperature at the space between the urine absorption member 102 and the body is lowered. But, before the lowered temperature at the space rises to the same temperature as the body temperature, if the temperature starts to fall for some reasons, erroneous detection that urine or feces has been discharged may be made based on the signal output from the back-side thermistor 145b. Therefore, in the automatic urine disposal apparatus 100, when determining whether feces has been discharged or not based on the signal output from the back-side thermistor 145b, the accuracy of determination of the presence of discharged feces increases by not using the signal, for the determination of defecation, which is output during a predetermined time after the operation of the suction pump 108b, for example, during 2 minutes after the operation.

Feces Detection Method

Figure 12:
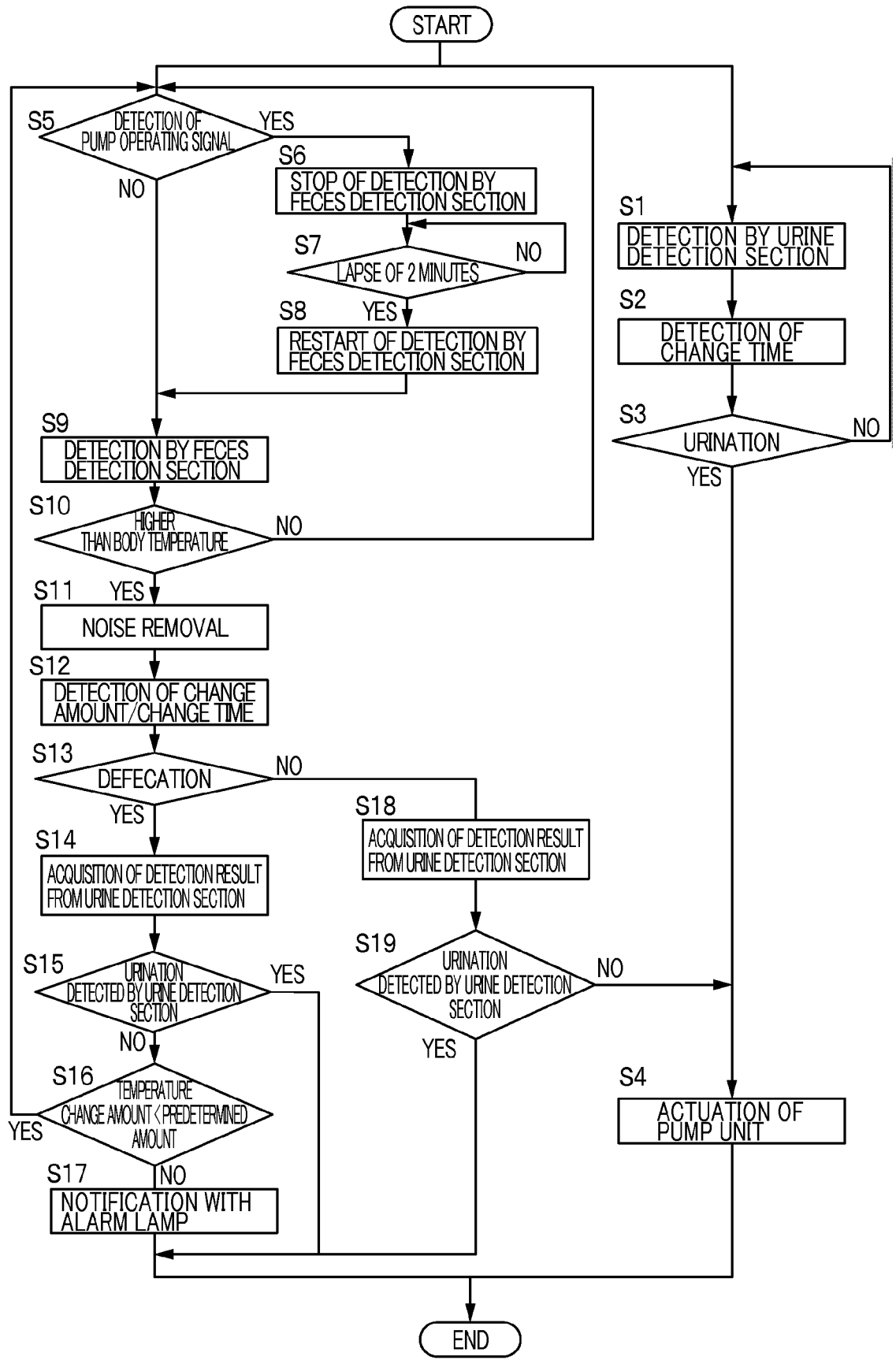
FIG. 12 is a flowchart showing a detection method of urination and defecation in the automatic urine disposal apparatus.

FIG. 12 is a flowchart showing a detection method of urination and defecation by the automatic urine disposal apparatus.

As shown in FIG. 12, in the defecation detection method of the automatic urine disposal apparatus 100 according to this embodiment, the control circuit 108a detects concurrently signals output from the urine detection electrodes 218a and 218b, the front-side thermistor 145a, and the back-side thermistor 145b. More specifically, the control circuit 108a of the pump unit 108 continuously or intermittently measures the followings: the electric resistance (impedance) between the urine detection electrodes 218a and 218b; and the changes in the electric resistances output from the thermistors 145a and 145b. Here, the control circuit 108a measures the changes in the electric resistances output from the front-side thermistor 145a and the back-side thermistor 145b synchronously at given time intervals. For example, signals which are detected by measuring the changes of the electric resistances per second for 5 minutes are processed as a unit. In addition, the measurings of the changes of the electric resistances start at the same point in time which is delayed by 1 second, and continue.

Also, the timer is actuated at a time when the automatic urine disposal apparatus 100 is switched on. Thereafter, every time when a lapse of 1 hour is detected with the timer, the control circuit 108a operates the suction pump 108b for about 1 minute.

If a signal for actuating the suction pump 108b is detected (S5), the automatic urine disposal apparatus 100 stops the detection of the signal that is output from the back-side thermistor 145b (S6). For example, when a signal for actuating the suction pump 108b is detected, the apparatus stops, during 2 minutes after the actuating signal stops, the detection of the signal that is output from the back-side thermistor 145b. Once the lapse of 2 minutes after the stop of the suction pump 108b is detected with the timer (S7), the detection of the signal that is output from the back-side thermistor 145b is restarted (S8). Note that the detection of the signal that is output from the urine detection section 102b continues (S1) irrespective of the detection of the signal for actuating the suction pump 108b. If the signal for actuating the suction pump 108b is not detected (S5), the signal that is output from the back-side thermistor 145b is continuously detected.

Thereafter, if a temperature rise is detected by the signal that is output from the back-side thermistor 145b (S9), it is determined whether or not the detected absolute temperature is higher than the body temperature, which is a predetermined temperature, for example, 36 degrees (S10). If the detected temperature is higher than the body temperature, the control circuit 108a executes the feces detection processing based on the results of 5-minute synchronized measurement of the subsequent changes in the electric resistances output from the front-side thermistors 145a and the back-side thermistors 145b. If the detected temperature is lower than the body temperature, the control circuit 108a determines that the temperature rise is not caused by defecation. Then, while the control circuit 108a is detecting whether the suction pump 108b is actuated or not (S5), the control circuit 108a continues the measurement the start time of which is delayed by 1 second every time.

Signals output from the urine detection section 102b are kept being detected during this period; when urine is discharged into the urine absorption member 102, the control circuit 108a detects that the electric resistance between the urine detection electrodes 218a and 218b has decreased (S1). With this detection of the decrease in the electric resistance between the urine detection electrodes 218a and 218b, the control circuit 108a detects the change in the electric resistance in a predetermined time. Then, when a stable output is resumed (S2), the control circuit 108a determines that this is the signal which indicates detection of discharge of urine (S3), and actuates the suction pump 108b (S4).

When the control circuit 108a detects a decrease in the electric resistance of the back-side thermistor 145b, that is, the circuit detects that the temperature rises to a temperature higher than or equal to the body temperature (S10), the control circuit 108a removes the data of the changes in electric resistance measured by the front-side thermistor 145a from the data of the changes in electric resistance measured by the back-side thermistor 145b for the 5 minutes of both data after the detection of the decrease in electric resistance (S11). Thus, a temperature change caused by other than defecation, in other words, noise, can be removed.

Thereafter, the control circuit 108a detects the course of the change in electric resistance in the noise-removed data, and calculates the rate at which the temperature falls, from the course of the electric resistance change (S12). For example, for the noise-removed 5-minute data, the control circuit 108a detects the temperature that has fallen in 2 minutes after the temperature rise has been detected based on the change in the electric resistance of the back-side thermistor 145b, to determine defecation or urination (S13). If the rate at which the electric resistance rises in the noise-removed data, that is, the rate at which the temperature falls, is slow, it is temporarily assumed that the signal indicates detection of discharge of feces. At this time, the detection result on the presence of urination is acquired, which is based on the electric resistance value between the urine detection electrodes 218a and 218b (S14). Then, if discharge of urine has already been detected (S15), it is determined that the excrement is urine, not feces, giving high priority to the detection result by the urine detection electrodes 218a and 218b. In this case, since the suction pump 108b is already operating, there is no need to actuate the suction pump 108b at this stage.

On the other hand, the control circuit 108a determines that the excrement is feces in the following case: it is temporarily assumed based on the noise-removed data that the signal indicates detection of discharge of feces (S8); the detection result on the presence of urination is acquired, which is based on the electric resistance value between the urine detection electrodes 218a and 218b (S14); and then discharge of urine has not been detected (S15).

When it is determined that it is feces that has been discharged, the control circuit 108a acquires a stored threshold which is for determination of the discharge amount, and compares the acquired threshold and the amount of the temperature rise by which the discharge of feces has been detected (hereinafter referred to as the temperature-rise amount at detection) (S16). If the temperature-rise amount at detection is greater than the threshold, the control circuit 108a determines that the amount of discharged feces is large and actuates the alarm lamp 504 (S17). On the other hand, if the temperature-rise amount at detection is smaller than the threshold, the control circuit 108a determines that the amount of discharged feces is small and continues the temperature detection without actuating the alarm lamp 504.

Further, if the rate at which the electric resistance rises in the noise-removed data, that is, the rate at which the temperature falls, is rapid, it is temporarily assumed that the signal indicates detection of discharge of urine (S13). At this time, the detection result on the presence of urination is acquired, which is based on the electric resistance value between the urine detection electrodes 218a and 218b (S18). Then, if discharge of urine has already been detected (S19), it is determined that the excrement is urine. In this case, since the suction pump 108b is operating, it is unnecessary for the control circuit 108a to actuate the suction pump 108b at this stage. On the other hand, if discharge of urine has not been detected from the detection result on the presence of urination based on the electric resistance value between the urine detection electrodes 218a and 218b (S19), the control circuit 108a actuates the suction pump 108b (S4).

In the automatic urine disposal apparatus 100 of this embodiment, when the suction pump 108b is operated, the presence of discharged feces is determined based on the signals remaining after removing data which corresponds to a 2-minute period after the operation of the suction pump 108b from signals which are output from the front-side thermistor 145a and the back-side thermistor 145b. Therefore, the determination of the presence of discharged feces is unaffected by the temperature change caused by the operation of the suction pump 108b. This makes it possible to correctly determine the presence of discharged feces. The suction pump 108b is actuated at periodical intervals as well as when discharge of urine has been detected by the urine detection section 102b. In both of the cases where the suction pump 108b is operated, the presence of discharged feces is determined based on the signals remaining after removing data which corresponds to 2-minute period after the operation of the suction pump 108b from signals which are output from the front-side thermistor 145a and the back-side thermistor 145b. Therefore, although the apparatus has the suction pump 108b, it can detect the presence of discharged feces correctly.

When the suction pump 108b is operated, outputs from the front-side thermistor 145a and the back-side thermistor 145b change significantly. Therefore, if the determination is made based on temperature change as measured with respect to temperature which has dropped significantly, the possibility of erroneous determination will be high. Also, the temperature of discharged feces is higher than the temperature of a human body. Therefore, when the absolute temperature detected by the front-side thermistor 145a and the back-side thermistor 145b is lower than the temperature of a human body (36 degrees), erroneous determination can be further prevented or reduced by performing no detection of the presence of discharged feces.

Feces and urine have a higher temperature than the body temperature at the time of discharge. However, feces and urine are different in the way temperature falls over time after discharge, that is, in the rate at which the temperature falls, because of the difference in heat capacity. Therefore, as in the automatic urine disposal apparatus 100 described above, the control section 108a determines that either urine or feces has been discharged, based on the rate at which the temperature falls after the detection of a rise of the temperature by the signal that is output from the back-side thermistor 145b placed in the urine absorption member 102. This makes it possible to more correctly determine whether it is urine or feces that have been discharged.

In the signal output from the back-side thermistor 145b, the detected temperature varies depending on the amount of discharged feces. For example, if the amount of feces is large, the detected temperature is high because the entire back-side thermistor 145b is covered with feces. On the other hand, if the amount of feces is small, the detected temperature is lower compared with the case of the large feces amount. This is because the back-side thermistor 145b is covered partly, or not covered at all, with feces. Therefore, as with the automatic urine disposal apparatus 100 described above, the following steps after the determining that feces has been discharged make it possible to determine, not only the presence of discharged feces, but also whether the amount of discharged feces is large or small: first detecting the temperature-rise amount based on the signal that is output from the back-side thermistor 145b; and then determining whether the discharged amount is large or small using the detected temperature-rise amount.

Moreover, since the skin-contact sheet 134 is placed on the side of the back-side thermistor 145b closer to the wearer, an air space is formed between the back-side thermistor 145b and the feces, which prevents discharged feces from coming into direct contact with the back-side thermistor 145b. Therefore, the signal output from the back-side thermistor 145b is likely to change depending on the amount of discharged feces. This makes it possible to more correctly determine the amount of discharged feces.

In particular, if employing a nonwoven fabric as the skin-contact sheet 134 which is placed between the back-side thermistor 145b and feces, an air space is formed between the skin-contact sheet 134 and feces. Therefore, when the amount of discharged feces is large, the air space is pressed down under the weight of the feces, permitting the temperature to be detected at a position where the back-side thermistor 145b is closer to the feces. On the other hand, when the amount of discharged feces is small, the temperature of the feces is detected over the air space. This makes it possible to more correctly detect whether the amount of discharged feces is large or small.

Also, the back-side thermistor 145b is placed at the defecation position of the urine absorption member 102. Therefore the back-side thermistor 145b is close to feces when the feces are discharged, which causes a rapid rise of the temperature. On the other hand, the front-side thermistor 145a is placed at a non-defecation position of the urine absorption member 102. Therefore, the front-side thermistor 145a does not come into contact with feces when the feces is discharged, which does not cause rapid rise of the temperature due to discharged feces. Moreover, since the back-side thermistor 145b and the front-side thermistor 145a are placed on the single urine absorption member 102, the thermistors undergo almost the same influence of a temperature change in the space between the urine absorption member 102 and the wearer's body, the temperature change being caused by other than defecation. Thus, the control circuit 108a detects the presence of defecation, based on the data remaining after the signal that is output from the front-side thermistor 145a has been removed from the signal that is output from the back-side thermistor 145b, the signal from the front-side thermistor 145a including a temperature change caused by other than defecation, the signal from the back-side thermistor 145b including a temperature change due to defecation and a temperature change caused by other than defecation. This makes it possible to detect defecation more correctly.

Since persons who need defecation detection are those who require nursing care such as bedridden elderly persons, for example, the automatic urine disposal apparatus 100 is used for such persons requiring care when lying on the bed. When a person requiring care discharges feces when lying on the bed, the feces will collect at a position lower than his or her body, that is, at the defecation position on the back side of the body. In addition, it is desirable that the front-side thermistor 145a capable of detecting a temperature change caused by other than defecation be placed at a position in a non-defecation position which is as close to the back-side thermistor 145b at the defecation position as possible and will not covered with feces. Therefore, by placing the front-side thermistor 145a at a position facing the groin or a position between the position facing the groin and the defecation position, the front-side thermistor 145a can be prevented from being covered with feces and can more reliably detect a temperature change caused by other than defecation in the front-side thermistor 145a. This makes it possible to more correctly detect defecation.

In addition, the front-side thermistor 145a and the back-side thermistor 145b are formed on the single insulating synthetic resin film 260. Therefore, the thermistors can be easily attached to the film without the necessity of attaching the front-side thermistor 145a and the back-side thermistor 145b separately. Also, the front-side thermistor 145a and the back-side thermistor 145b are formed on the insulating synthetic resin film 260, which is on the thin and flexible. Therefore, the user can use the apparatus without discomfort.

When detecting defecation, the control circuit 108a of the automatic urine disposal apparatus 100 actuates the alarm lamp 504 for notification of the defecation. Therefore, when defecation has occurred, it is possible to give notification of the defecation to the caregiver, for example. At this time, if the alarm lamp 504 is actuated even when feces is discharged but the discharged amount is too small to require replacement of the urine absorption member 102, the caregiver will have to replace the urine absorption member 102 when actually replacement is unnecessary. Thus, the alarm lamp 504 is not actuated when the amount of feces is too small to require replacement of the urine absorption member 102. This makes it possible to reduce the burden on the caregiver, etc.

Since the urine detection section 102b includes the pair of urine detection electrodes 218a and 218b placed on the insulating synthetic resin film 260 with spacing therebetween, the function of detecting urine can be achieved at low cost. Also, since the pair of urine detection electrodes 218a and 218b are placed on the thin, flexible, insulating synthetic resin film 260, the user can use the apparatus without discomfort. Moreover, the presence of urine increases the conductivity of the pair of urine detection electrodes 218a and 218b with spacing therebetween. This makes it possible to more reliably detect urine by detecting urine based on a change in the voltage between the urine detection electrodes 218a and 218b.

Other Embodiments

While the automatic urine disposal apparatus is described as the defecation detection apparatus of the present invention with reference to the preferred embodiment, the embodiment is for the purpose of elucidating the understanding of the invention and is not to be interpreted as limiting the invention. The invention can of course be altered and improved without departing from the gist thereof, and equivalents are intended to be embraced therein.

In the above embodiment, there is described an example in which the suction pump 108b is actuated periodically irrespective of the urine suction operation which is performed after urination. However, the invention is not limited to thereto. The suction pump 108b may be actuated 1 hour after the suction pump 108b operated and stopped the previous time.

In the above embodiment, there is described an example of having two temperature sensors: the front-side thermistor 145a and the back-side thermistor 145b. Alternatively, a form of having only the back-side thermistor 145b which is placed at the defecation position may be employed. In this case, noise removal processing is not executed.

In the above embodiment, there is described an example using two temperature sensors: the front-side thermistor and the back-side thermistor. The present invention is not limited thereto. For example, a defecation-position thermistor and a non-defecation-position thermistor are defined as follows: a plurality of thermistors are provided in the electrode unit along the length direction and detect signals that are output from the thermistors; in the case where there is detected a temperature change where the temperature rapidly rises and then slowly falls, the thermistor which has detected this temperature change is defined as the defecation-position thermistor which is placed at the defecation position; and the thermistor which is closest to the defecation-position thermistor and has not detected this temperature change, rapid rise and slow fall, is defined as the non-defecation-position thermistor which is placed at a non-defecation position. The presence of defecation may be detected by removing the signal that is output by the non-defecation-position thermistor from the signal that is output by the defecation-position thermistor. In this case, since the non-defecation-position thermistor is placed closer to the defecation position, noise can be removed more correctly, permitting more correct detection of the presence of defecation.

DESCRIPTION OF REFERENCE NUMERALS 100 automatic urine disposal apparatus (defecation detection apparatus)
100a vacuum suction device (urine suction device)
101 controller
102 urine absorption member
102a container section (feces/urine receiving member)
102b urine detection section
102c exposed portion
104 joint member
106 urine guide tube
106a urine tank
108 pump unit
108a control circuit (control section)
108b suction pump
112 container
114 urine drainage port
116 electrical wiring
116a power supply
118 electrode unit
120 clip
124 hardly-air-permeable sheet
126 diffusion sheet
128 cushion sheet
130 spacer
132 filter
134 skin-contact sheet (sheet material)
136 leakage barrier
136a sheet
136b elastic member
136c outer edge portion
136d inner edge portion
138 end sheet
140 end sheet
143a power supply electrode
143b power supply electrode
143c power supply electrode
145 thermistor
145a front-side thermistor (second temperature sensor)
145b back-side thermistor (first temperature sensor)
150 detection section
152 peripheral flange
169a uncoated portion
170 insulating coating
171 opening
218a urine detection electrode (pair of electrodes)
218b urine detection electrode (pair of electrodes)
250 break detection circuit
260 film
265 connecting portion
266 top end portion
267a side portion
267b side portion
268 bottom end portion
300 pants
301 front waist region
302 back waist region
303 crotch region
504 alarm lamp (notification section)

The invention claimed is:
1. A defecation detection apparatus comprising:
a feces/urine receiving member that is placed to face the body of a wearer and that receives discharged feces and urine;
a urine suction device that is detachably attached to the feces/urine receiving member and that can suck urine discharged in the feces/urine receiving member;
a temperature sensor that is placed at a defecation position where discharged feces are received in the feces/urine receiving member; and
a control section that detects the presence of discharged feces based on a signal remaining after removing a signal that is output from the temperature sensor within a predetermined time after an operation of the urine suction device from a signal that is output from the temperature sensor, wherein based on a rate at which a temperature falls after detecting a rise of the temperature by the signal that is output from the temperature sensor, the control section determines whether at least one of urine and feces has been discharged.

2. A defecation detection apparatus according to claim 1, wherein the apparatus further comprises a urine detection section that detects urine discharged in the feces/urine receiving member, and when the urine detection section detects urine, the control section operates the urine suction device and the urine suction device sucks the urine in the feces/urine receiving member.

3. A defecation detection apparatus according to claim 1, wherein the control section operates the urine suction device periodically.

4. The defecation detection apparatus according to claim 1, wherein when an absolute temperature detected by the temperature sensor is lower than a predetermined temperature, the control section does not detect the presence of discharged feces.

5. A defecation detection apparatus according to claim 4, wherein the predetermined temperature is a temperature of a human body.

6. A defecation detection apparatus according to claim 1, wherein after determining that feces has been discharged, the control section detects an amount of the temperature rise based on the signal that is output from the temperature sensor, and determines whether an amount of the discharged feces is large or small, using the rise amount.

7. A defecation detection apparatus according to claim 1, wherein the temperature sensor is covered with a sheet material, and a temperature of feces is detected over the sheet material.

8. A defecation detection apparatus according to claim 7, wherein the sheet material is a nonwoven fabric.

9. A defecation detection apparatus according to claim 1, wherein the apparatus further comprises a first temperature sensor that is placed at a defecation position in the feces/urine receiving member where discharged feces are received, and a second temperature sensor that is placed at a non-defecation position in the feces/urine receiving member where discharged feces are not received, and the control section determines whether it is urine or feces that has been discharged, based on a signal remaining after a signal that is output from the second temperature sensor has been removed from a signal that is output from the first temperature sensor.

10. A defecation detection apparatus according to claim 9, wherein the second temperature sensor is placed at a position facing the groin when the feces/urine receiving member faces the body or at a position between the position facing the groin and the defecation position.

11. A defecation detection apparatus according to claim 9, wherein the first temperature sensor and the second temperature sensor are formed on a single insulating synthetic resin film.

12. A defecation detection apparatus according to claim 1, wherein the apparatus further comprises a notification section that notifies that feces has been discharged, and when it is determined that feces has been discharged, the control section operates the notification section.

13. A defecation detection apparatus according to claim 12, wherein the control section does not operate the notification section when it is determined that an amount of the discharged feces is smaller than a predetermined amount.

14. A defecation detection apparatus according to claim 11, wherein the urine detection section is a pair of electrodes formed on the insulating synthetic resin film with spacing therebetween, and discharge of urine is detected based on a change in voltage between the pair of electrodes, the change being caused by discharged urine.

* * * * *